United States Patent
Sharma et al.

(10) Patent No.: US 10,474,917 B2
(45) Date of Patent: Nov. 12, 2019

(54) SMART EDITING OF IMAGE-PROCESSING RESULTS

(71) Applicant: Siemens Healthcare GmbH, Erlangen (DE)

(72) Inventors: Puneet Sharma, Monmouth Junction, NJ (US); Tiziano Passerini, Plainsboro, NJ (US); Mehmet Akif Gulsun, Lawrenceville, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 184 days.

(21) Appl. No.: 15/715,604

(22) Filed: Sep. 26, 2017

(65) Prior Publication Data

US 2019/0095738 A1    Mar. 28, 2019

(51) Int. Cl.
  *G06K 9/03*    (2006.01)
  *G06K 9/32*    (2006.01)
  *G06K 9/34*    (2006.01)
  *G06K 9/66*    (2006.01)

(52) U.S. Cl.
  CPC ........... *G06K 9/033* (2013.01); *G06K 9/3233* (2013.01); *G06K 9/34* (2013.01); *G06K 9/66* (2013.01); *G06K 2209/05* (2013.01)

(58) Field of Classification Search
  CPC .. G06K 2209/05; G06K 9/033; G06K 9/3233; G06K 9/34; G06K 9/66; G06T 2207/10116; G06T 2207/20081; G06T 2207/20084; G06T 2207/30101; G06T 7/11; G16H 30/40
  See application file for complete search history.

(56) References Cited

U.S. PATENT DOCUMENTS

| | | | |
|---|---|---|---|
| 2006/0007244 A1* | 1/2006 | Matsumoto | G06F 19/321 345/619 |
| 2010/0111386 A1* | 5/2010 | El-Baz | G06T 7/0016 382/128 |
| 2017/0103512 A1 | 4/2017 | Mailhe et al. | |

FOREIGN PATENT DOCUMENTS

WO    2017093337 A1    6/2017

OTHER PUBLICATIONS

Extended European Search Report (EESR) dated Feb. 18, 2019 in corresponding European Patent Application No. 18195905.7.
(Continued)

*Primary Examiner* — Nirav G Patel

(57) ABSTRACT

A computer-implemented method for editing image processing results includes performing one or more image processing tasks on an input image using an iterative editing process. The iterative editing process is executed until receiving a user exit request. Each iteration of the iterative editing process comprises using a first machine learning model to generate a plurality of processed images. Each processed image corresponds to a distinct set of processing parameters. The iterative editing process further comprises presenting the plurality of processed images to a user on a display and receiving a user response comprising (i) an indication of acceptance of one or more of the processed images, (ii) an indication of rejection of all of the processed images, or (iii) the user exit request. Following the iterative editing process clinical tasks are performed using at least one of the processed images generated immediately prior to receiving the user exit request.

18 Claims, 5 Drawing Sheets

(56) References Cited

OTHER PUBLICATIONS

Anonymous: "Supervised learning—Wikipedia"; Wikipedia, Sep. 25, 2017; XP055551926; Retrieved from the Internet: URL:https ://en.wikipedia .org/w/index.php?title=Supervised learning&oldid=802294351; retrieved on Feb. 5, 2019.

Anonymous: "Image segmentation—Wikipedia"; Wikipedia, Sep. 14, 2017; XP055553299; Retrieved from the Internet: URL:https://en.wikipedia . org/w/index.php?title=Image segmentation&oldid=800585998; retrieved-on Feb. 7, 2019.

* cited by examiner

SMART EDITING OF IMAGE-PROCESSING RESULTS

TECHNICAL FIELD

The present invention relates generally to methods, systems, and apparatuses for editing imaging processing results using machine learning techniques. The technology described herein may be applied, for example, to processing medical images in clinical and interventional settings.

BACKGROUND

Medical image processing tasks such as detection, classification, segmentation, and registration are integral parts of image post-processing workstations. When a user has to perform some kind of editing of the results, he/she typically uses the input device (e.g., the mouse or a stylus) to either draw/re-draw contour, or move/drag contours to accomplish the editing task.

In a busy clinical workflow, it is not always possible to perform detailed and tedious editing. For example: in an interventional setting with a sterile environment, it is not always possible to perform editing in a manner similar to the one on a post-processing workstation. Typically, the interventional clinician has access to a joystick controller on the C-arm system to accomplish all his/her tasks without disrupting the workflow. This joystick is not as versatile as the mouse or stylus for editing contours in 2D or 3D. Another example is in the scan room where a technician might want to edit the results of an automatic algorithm (e.g., an "inline" algorithm on a Magnetic Resonance scanner, or a "PACS-ready" algorithm on a Computed Tomography scanner). In such a scenario, the user may not have access to all the advanced editing tools that are typically present on a 3D post-processing workstation. As a result, there is a need for smart editing algorithms that do not require a clinician to use a mouse or a stylus. Additionally, there exists a large amount of inter-user variability when users are given access to free-hand editing tools.

Currently, image editing is typically performed by a user in either a purely manual or a semi-automatic fashion by using an input device such as a computer mouse or a pen/stylus. Such tools are routinely available on all image post-processing workstations. Because this is not always possible in an interventional suite, the user typically has to either instruct a technician to perform these tasks on a workstation that is outside the operating room (e.g., in the control room), or has to disrupt their workflow at the table-side to perform this themselves.

SUMMARY

Embodiments of the present invention address and overcome one or more of the above shortcomings and drawbacks by providing methods, systems, and apparatuses related to the smart editing of images using machine learning models.

According to some embodiments, a computer-implemented method for editing image processing results includes performing one or more image processing tasks on an input image using an iterative editing process. The iterative editing process is executed until receiving a user exit request. Each iteration of the iterative editing process comprises using a first machine learning model to generate a plurality of processed images. Each processed image corresponds to a distinct set of processing parameters. The iterative editing process further comprises presenting the processed images to a user on a display and receiving a user response comprising (i) an indication of acceptance of one or more of the processed images, (ii) an indication of rejection of all of the processed images, or (iii) the user exit request. Following the iterative editing process, clinical tasks are performed using at least one of the processed images generated immediately prior to receiving the user exit request.

The image processing tasks used in the aforementioned method may include one or more of a segmentation of an anatomical object of interest from the input image, a detection of one or more clinical indicators of interest present in the input image, tracking of one or more objects of interest present in the input image, registering the input image to one or more other images, or classifying the input image with one or more classification labels.

In some embodiments of the aforementioned method, the iterative editing process further includes using the processed images and the user response to train a second machine learning model to generate first model input parameters to the first machine learning model. During the iterative editing process, the first model input parameters may be used as input to the first machine learning model. In some embodiments, the second machine learning model is used to identify a most desirable option from among the processed images, and the processed images are presented to the user on the display with a visual indication of the most desirable option. In other embodiments, the second machine learning model is used to sort the processed images based on user preference, and the processed images are presented to the user on the display in a sorted order. In some embodiments, a region of interest is identified within the input image, and the first machine learning model is only applied to image data within the region of interest when generating the processed images. This region of interest may be identified manually, for example, based on user selection of a region of the input image or automatically, for example, using the second machine learning model.

According to other embodiments of the present invention, a computer-implemented method for processing an image includes receiving one or more images acquired from an image scanner device and automatically generating an initial segmentation of an anatomical feature of interest by applying a segmentation algorithm to the image. Next, the initial segmentation is presented to a user on a display and, in response to receiving a rejection of the initial segmentation from the user, an iterative segmentation process is performed until a user exit request is received. The iterative segmentation process includes generating a plurality of alternative segmentations of the anatomical feature of interest by applying a first machine learning model to the images using a plurality of first model parameters. The iterative segmentation process further includes presenting the alternative segmentations to the user on the display and receiving a user response comprising (i) an indication of acceptance of one or more of the alternative segmentations, (ii) an indication of rejection of all of the alternative segmentations, or (iii) the user exit request. Then, the first model parameters are updated based on the user response.

According to other embodiments of the present invention, a system for processing images comprises a display, one or more processors; and a non-transitory, tangible computer-readable medium. This medium holds instructions executable by the processors for performing one or more of the methods discussed above.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings exemplary embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses related to smart editing of images. The techniques described herein are generally capable of editing the results produced by any kind of image processing algorithms. These techniques do not require the user to actively draw, edit or manipulate structures (e.g., points, lines, contours, surfaces etc.) using a standard input device (e.g., a mouse or a touch stylus), but instead guide the user through a simple workflow that presents a series of options that are prepared on-the-fly based on user's current state.

A "smart editing" technique fits the workflow in an interventional setting where the clinician (referred to herein as the "user") is typically operating on a patient in a sterile environment, and cannot have access to the traditional image processing tools that are used for performing image processing tasks segmentation and editing. The smart editing approach is based on using a set (one of more) of machine learning algorithms that are activated on-the-fly when the user prompts the system that they would like to edit the result of the image processing algorithm (e.g., the segmentation of an anatomical object).

Figure 1:
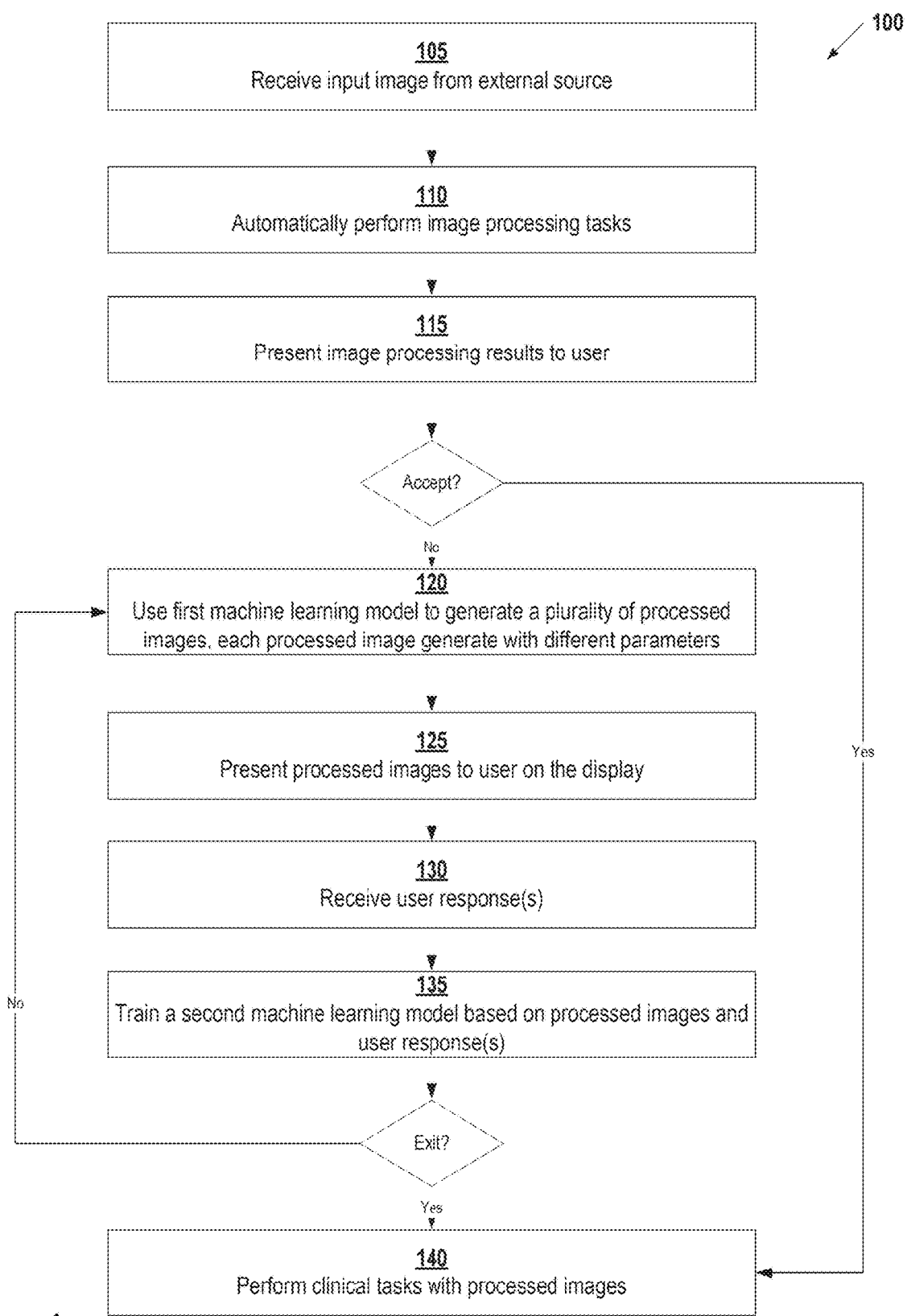
FIG. 1 shows a smart editing method, according to some embodiments of the present invention.

FIG. 1 shows a smart editing method 100, according to some embodiments of the present invention. This method 100 may generally be performed on any computing system; however, some computing architectures may provide certain advantages for processing or convenience. For example, for the diagnostic imaging use cases, the method 100 could be readily applied to the use cases that are executed on the scanner (e.g., the PACS-ready technology results on the CT scanner, or the "inline" functionality on the MRI scanner). Additionally, the smart editing can be readily parallelized as described below with respect to FIG. 5.

Starting at step 105, the system performing the method 100 receives an input image from an external source. In some embodiments, the external source is an image scanner device such as a Computed Tomography Scanner, a Magnetic Resonance Scanner, or an X-ray angiography scanner. The system performing the method 100 may be directly connected to the external source such that the image can be received immediately following acquisition. Alternatively, following acquisition, the image may be stored for later retrieval and processing by the method 100. It should also be noted that, although the method 100 is described herein with respect to a single image, the method 100 may be generalized to process multiple images. For example, in some embodiments, a stream of images is received and processed using the method 100.

At step 110, one or more image processing tasks are automatically performed on the input image. In general any type of image processing task may be performed. Example tasks include segmentation of an anatomical object of interest from the input image; detection of one or more clinical indicators of interest present in the input image; tracking of one or more objects of interest present in the input image; registering the input image to one or more other images; or classifying the input image with one or more classification labels. Techniques for automating image processing are generally known in the art and, thus, are not described herein in detail. The exact processing that occurs will depend on the desired tasks that need to be performed. For example, if the image processing task is image segmentation, an automated segmentation process may be performed (with or without input from the user). Similarly, if the tasks include image registration, an automatic registration algorithm may be executed on the input image and one or more additional images. Additionally, depending on the desired image processing results, different techniques may be combined.

Following the execution of step 110, the initial processed image is presented on a display for the user to review at step 115. In some embodiments, the display is directly connected to the computing system performing the method 100. In other embodiments, the display may be on a different computing device than the system performing the method 100 (e.g., in a cloud-based computing implementation). The initial processed image is effectively the results of conventional image processing. Thus, it does not include the "smart editing" features described below which personalize the image processing tasks. The image is presented to the user in a graphical user interface (GUI) that allows the user to accept or reject the initial processed image. For example, in one embodiment, the GUI includes buttons labeled "Accept" and "Reject," indicating acceptance or rejection, respectively, of the initial processed image. If the user accepts the initial processed image, the workflow can continue and one or more clinical tasks can be performed using the initial processed image. However, if the user rejects the initial processed image, the method 100 continues to step 120. It should be noted that step 115 only requires basic user input; for example, it does not necessarily require the use of the mouse or a stylus, and can be easily performed with a joystick or a touch display.

At steps 120-135, in response to receiving a rejection of the initial processed image from the user, one or more image processing tasks are performed on the input image using an iterative editing process. Starting at step 120, a first machine learning model is used to generate a plurality of processed images. Each processed image corresponds to a distinct set of processing parameters. The first model could be a machine learning based model that has been trained for the purpose of generating multiple parameterization of the input processing task. In another embodiment, the first algorithm could be the same as the one that produced the original processing result at step 110, except with a different configuration (e.g. parameters internal to the algorithm). In a trivial case of image segmentation, the first model could be just dilation and/or erosion operation applied on the results of the original segmentation results.

Similar to step 115 above, at step 125, the plurality of processed images are presented to a user on a display. Note that, in contrast to step 115 where only one image is presented, at step 125, multiple images are presented. However, the same interface may be employed for both steps 115 and 125. That is, the processed images can be presented in a GUI that allows the user to interact with the images through mouse clicks, joystick movement, etc.

At step 130, a user response is received to the presentation made at step 125. This response may include, for example, acceptance of one or more of the processed images, rejection of all of the processed images, or a request to exit the iterative editing process (not depicted in FIG. 1). Acceptance of the images may be indicated, for example, by selecting one or more of the presented images (e.g., by clicking on the images themselves or by selecting a checkbox). Rejection may be indicated by not selecting any images or by selecting a particular GUI element (e.g., similar to the "Rejection" button described above). If the images are all acceptable, or the user otherwise wishes to terminate the iterative editing process, the user can select a GUI element corresponding to an exit request (e.g., an "Exit" button). However, if all the images are rejected, the iterative editing process will continue for another iteration (processing the input image with different parameters).

As the last step in the iterative editing process, at step 135, the processed images and the user response are used to train a second machine learning model. By learning from the user's feedback to presented images, over time the user's preferences can be learned. The second machine learning model may optionally be used to fine-tune the options that are subsequently shown to the user either for the same case (patient) or for a different case in the future. For example, the second machine learning model may generate user-specific first model input parameters to the first machine learning model. Ultimately, once fully trained, the second machine learning model may be used in conjunction with the first learning model to perform the image processing tasks without any user interaction at all.

In some embodiments, anatomy-specific model input parameters may be generated as an alternative to, or in addition to the user-specific model input parameters. For example, the model can be trained with image sequences labeled by what main anatomical structure can be seen in the image. In this case, the system would learn the common behavior across users to segment specific anatomy model input parameters. Similarly, the techniques described herein may be adapted to learn the optimal sequence for any class of images, as long as the labels are provided in the training database.

Even before it is fully trained, the second machine learning model may be used to enhance the iterative editing process. For example, in one embodiment, the second machine learning model is used to identify a most desirable option among the processed images. The processed images may then be presented to the user in the GUI with a visual indication (e.g., colored outline) indicating the most desirable option. In other embodiments, the second machine learning model is used to sort the processed images based on user preference. Then, the processed images may be presented in the GUI in a sorted order (e.g., most preferable to least preferable).

The second machine learning algorithm could be any machine learning based algorithm (e.g., a deep reinforcement learning based algorithm, henceforward referred to as DRL) that has been trained offline to learn an optimal policy for editing the results of certain image processing tasks. Such an optimal policy can also be seen as an optimal trajectory that a user has to follow in order to reach the desired result (ground-truth). In the example presented in FIG. 1, the trajectory will be represented by the set of choices that a user selects at each step of the proposed editing workflow. In some embodiments, the DRL algorithm is trained using a plurality of training examples (i.e., trajectories) generated by one or more users who have performed the detailed editing task using standard input devices (e.g., as a mouse or a stylus), or by the proposed system. In other embodiments, the DRL algorithm may be trained "synthetically", i.e., by creating examples by using one or more image processing algorithm(s). Combinations of real and synthetic data may also be used for training of the DRL algorithm in some embodiments.

Returning to FIG. 1, the smart editing method 100 shows the iterative editing process as a loop performed over steps 120-135. Although the training of the second machine learning model is shown in this example as being included in the loop, it should be noted that, in some embodiments, the second machine learning model is trained outside of the loop (e.g., at a different time from execution of the other steps).

At step 140, the iterative editing process has been terminated and the user is satisfied with the processed images generated immediately prior to receiving the user exit request. Thus, one or more clinical tasks may be performed using those images. For example, the processed images may be used to study certain anatomical features or guide surgical procedures. In some embodiments, the processed images may be used as input into other automated routines to perform tasks such as disease detection.

Figure 2:
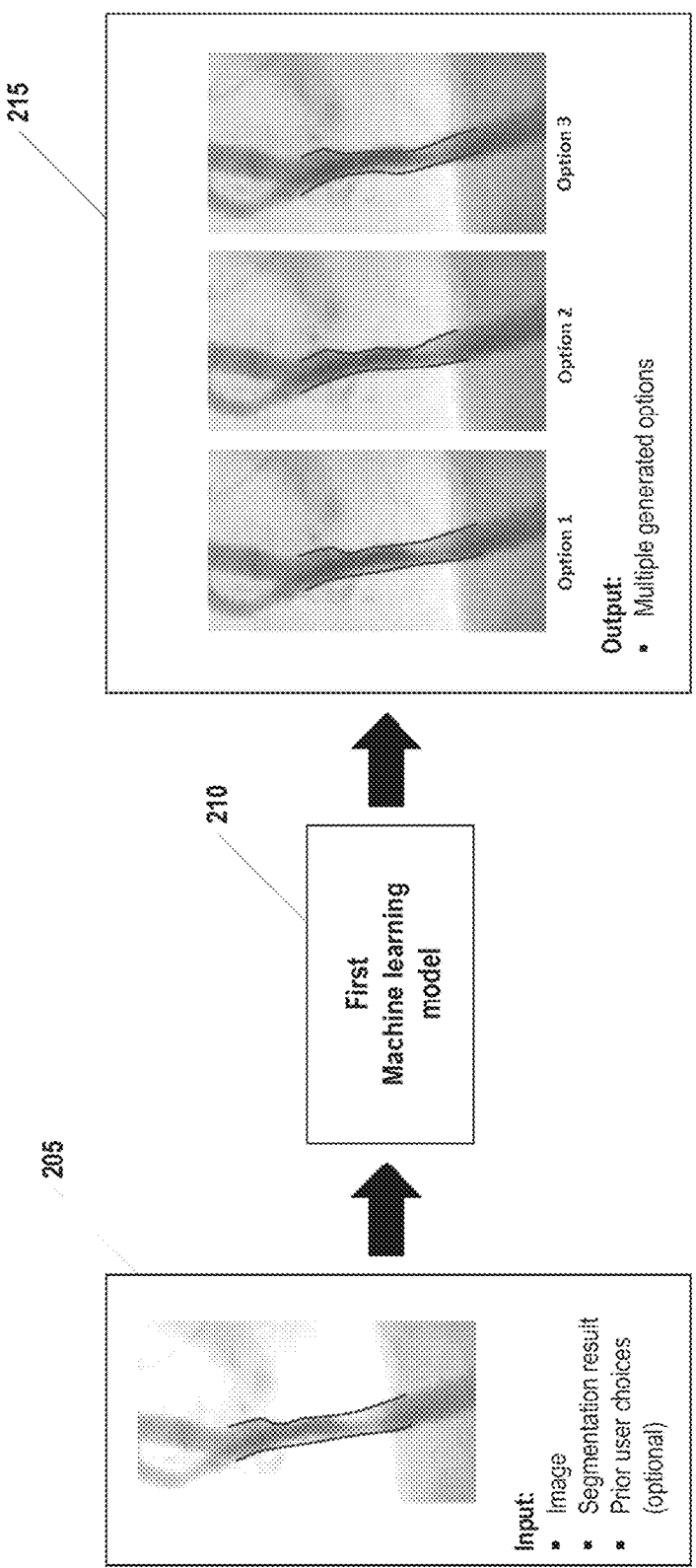
FIG. 2 provides an illustration of an example of the smart editing procedure, as it may be implemented in some embodiments.

FIG. 2 provides an illustration of an example of the smart editing procedure, as it may be implemented in some embodiments. In this example, the user would like to quantify the geometry of a coronary artery that has been imaged via invasive X-ray angiography. One of the constraints is that the user is equipped with a table-side control (i.e., a joystick) that can be used for basic manipulation. The user is first presented with the results of a segmentation algorithm 205, in form a vessel boundary. Next, the user indicates his/her preference (i.e., whether they accept the result as-is, or would like to edit it). This could be shown on the screen as a dialog with two options ("Accept" or "Edit"), or some variant of this. If the user chooses the "Edit" option, then the first machine learning algorithm 210 computes three candidates for an edited segmentation 215. These three candidates are then presented to the user. Note that the number of options is not limited to three, and could be either higher or lower. The user can again use a joystick to choose one of these three options, and terminate this workflow when he/she is satisfied that the segmentation shown on the screen is appropriate for the clinical task. Because all the options and user choices are being tracked, the second machine learning algorithm can use the user's response to generate a different set of options the next time the same user (or a different user) chooses to edit a particular segmentation result. This is possible because the second machine learning algorithm is trained specifically to learn the user behavior, specifically related to what they expect from a segmentation algorithm.

In some embodiments, the user may want to limit the editing action to a specific segmented object in a multi-body segmentation problem; or to a specific component of the segmentation (e.g., a single landmark position; a single border; a single surface; etc.). In this case, the system could prompt the user with a list of possible choices on screen, highlighting a single object available for editing. For example, the user may be first presented with the option of editing the first border of the vessel, the second border, or both jointly. Actions to modify the view can be provided, for example, via joystick or touch inputs on a touch screen. The first machine learning algorithm may then be used to propose multiple editing choices for the specific object of interest. Different machine learning algorithms could be designed for the first step (multiple choice of candidate segmentation results), specialized by the type of object of interest (e.g., landmark; border; shape; etc.).

To optimize the editing workflow, in some embodiments, the smart editing system supports selection of a region of interest (ROI) where to apply editing. In one embodiment, the ROI is defined as a box within the image (a rectangle for 2D images) that the user can manipulate by activating the joystick. For instance, joystick movements (UP-DOWN-LEFT-RIGHT) could correspond to movements of the box within the image, in the plane normal to the camera view. Other manipulation options could be associated to other joystick inputs: e.g., rotation of the joystick knob could be associated to scaling the size of the box, or to rotation of the box. Pushing the knob could be associated to selection of the current ROI and activation of the editing pipeline as described above. The first machine learning algorithm described above may then be applied only to the ROI and not to the entire image. In another embodiment, the user defines the ROI as the current view on screen. User actions modify the current view (zoom in/out, panning, rotation) to be focused on the area where editing should occur. Actions to modify the view can be provided via joystick or via e.g. touch inputs on a touch screen. Multi-finger gestures can be associated to different view manipulation actions (pinch for zoom, etc.).

The selection of the ROI can be suggested by applying the second machine learning algorithm as described above. To support this use case, the second machine learning algorithm may be trained including the selection of a ROI among the allowed user actions toward defining the optimal policy for editing.

Figure 3:
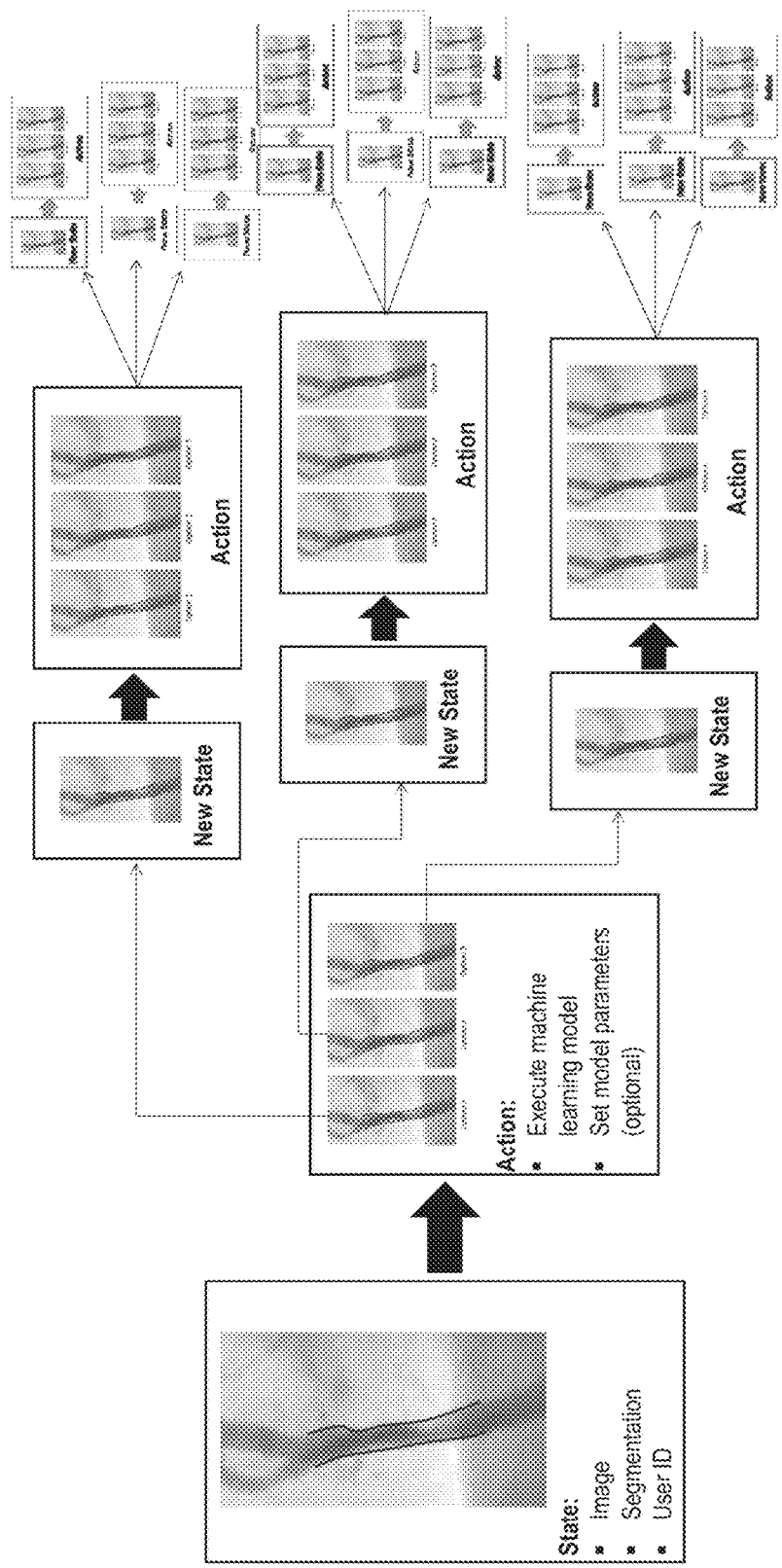
FIG. 3 illustrates one technique for generating a training database for training the second machine learning model discussed above, according to some embodiments.
Figure 4:
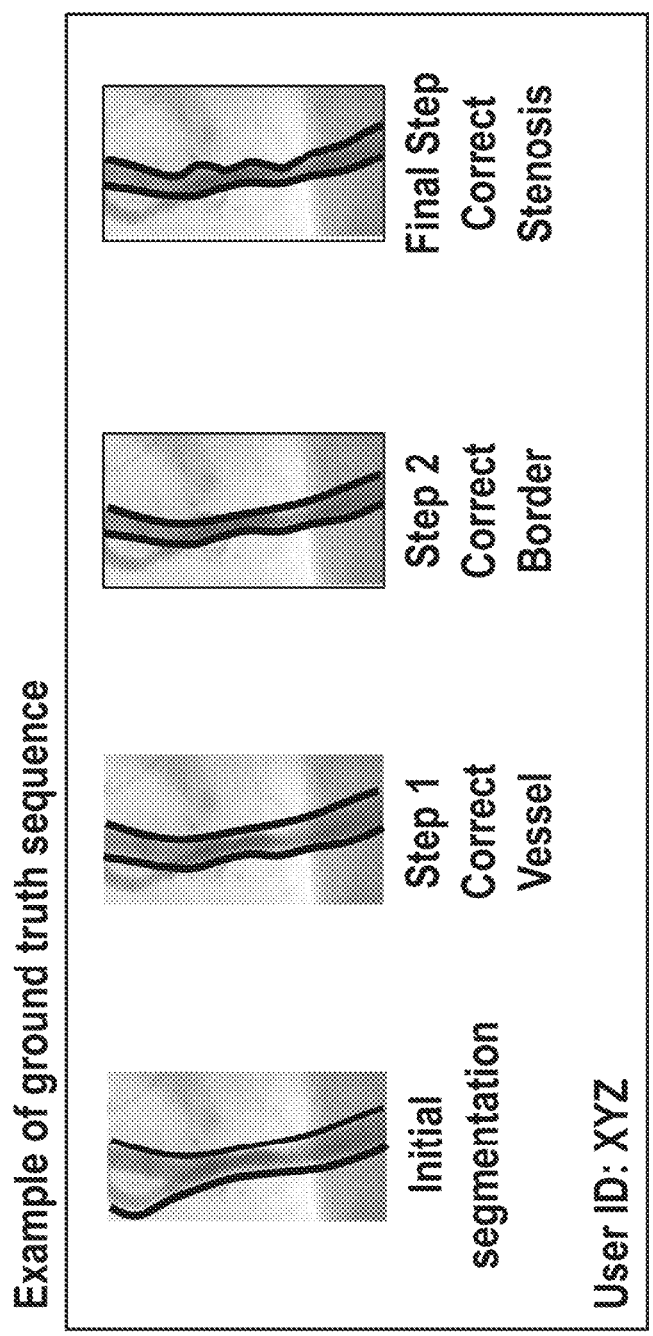
FIG. 4 shows an example ground truth sequence for use by the technique illustrated in FIG. 3.
Figure 5:
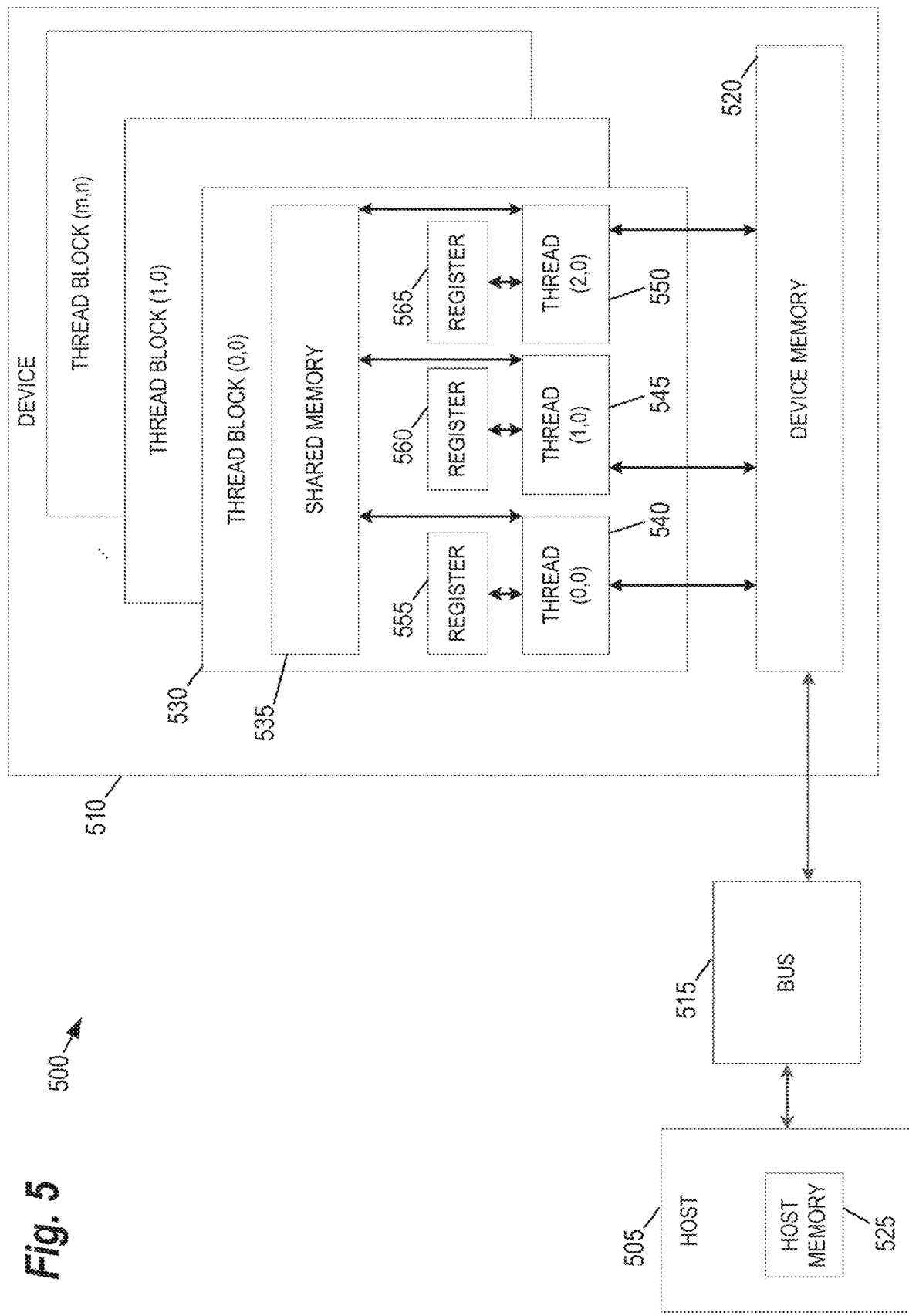
FIG. 5 provides an example of a parallel processing memory architecture that may be utilized to implement the machine learning models and other aspects of the various smart editing methods discussed herein.

FIG. 3 illustrates one technique for generating a training database for training the second machine learning model discussed above, according to some embodiments. In this example, it is assumed that the second machine learning model is a reward-based model. Additionally, this example, describes training with respect to a segmentation task; however, it should be understood that similar training techniques may be similarly applied for other image processing tasks. The starting point for training is an initial segmentation of an anatomical feature of interest in an image. The ground truth is the sequence of segmentation options (including the final segmentation) accepted by user, together with a user identifier ("ID"). FIG. 4 provides an example ground truth sequence. The training policy is to select the machine learning model (and its settings) so that the proposed options allow the shortest path to the final segmentation. The rewards set at each stage penalize increasing number of steps and reward proposed options being close to any of the ground truth states. The terminal state is a segmentation close to ground truth final segmentation FIG. 5 provides an example of a parallel processing platform 500 that may be utilized to implement the machine learning models and other aspects of the various workflows discussed herein. This platform 500 may be used in embodiments of the present invention where NVIDIA CUDA™ (or a similar parallel computing platform) is used. The architecture includes a host computing unit ("host") 505 and a graphics processing unit (GPU) device ("device") 510 connected via a bus 515 (e.g., a PCIe bus). The host 505 includes the central processing unit, or "CPU" (not shown in FIG. 5), and host memory 525 accessible to the CPU. The device 510 includes the graphics processing unit (GPU) and its associated memory 520, referred to herein as device memory. The device memory 520 may include various types of memory, each optimized for different memory usages. For example, in some embodiments, the device memory includes global memory, constant memory, and texture memory.

Parallel portions of a big data platform and/or big simulation platform may be executed on the platform 500 as "device kernels" or simply "kernels." A kernel comprises parameterized code configured to perform a particular function. The parallel computing platform is configured to execute these kernels in an optimal manner across the platform 500 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the platform 500 of FIG. 5 (or similar architectures) may be used to parallelize portions of the model based operations performed in training or utilizing the smart editing processes discussed herein. For example, in embodiments where a convolutional neural network is used as the machine learning model, the platform 500 can be used to perform operations such as forward and backward convolution, pooling, normalization, etc. Additionally, the parallel processing platform 500 may be used to execute multiple instances of a machine learning model in parallel. For example, multiple instances of the first machine model described above with respect to FIG. 1 may be executed in parallel with different parameters to simultaneously generate the plurality of options that the user is presented with (see step 120 in FIG. 1).

The device 510 includes one or more thread blocks 530 which represent the computation unit of the device 510. The term thread block refers to a group of threads that can cooperate via shared memory and synchronize their execution to coordinate memory accesses. For example, in FIG. 5, threads 540, 545 and 550 operate in thread block 530 and access shared memory 535. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 5, the thread blocks 530 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 5, registers 555, 560, and 565 represent the fast memory available to thread block 530. Each register is only accessible by a single thread. Thus, for example, register 555 may only be accessed by thread 540. Conversely, shared memory is allocated per thread block, so all threads in the block have access to the same shared memory. Thus, shared memory 535 is designed to be accessed, in parallel, by each thread 540, 545, and 550 in thread block 530. Threads can access data in shared memory 535 loaded from device memory 520 by other threads within the same thread block (e.g., thread block 530). The device memory 520 is accessed by all blocks of the grid and may be implemented using, for example, Dynamic Random-Access Memory (DRAM).

Each thread can have one or more levels of memory access. For example, in the platform 500 of FIG. 5, each thread may have three levels of memory access. First, each thread 540, 545, 550, can read and write to its corresponding registers 555, 560, and 565. Registers provide the fastest memory access to threads because there are no synchronization issues and the register is generally located close to a multiprocessor executing the thread. Second, each thread 540, 545, 550 in thread block 530, may read and write data to the shared memory 535 corresponding to that block 530. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 510 to read and/or write to the device memory. Device memory requires the longest time to access because access must be synchronized across the thread blocks operating on the device. Thus, in some embodiments, image data can be divided into segments using data locality techniques generally known in the art. Then, each segment can be processed in parallel using register memory, with shared and device memory only being used as necessary to combine the results to provide the results for the complete dataset.

The embodiments of the present disclosure may be implemented with any combination of hardware and software. For example, aside from parallel processing architecture presented in FIG. 5, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method for editing image processing results, the method comprising:
    performing one or more image processing tasks on an input image using an iterative editing process, wherein the iterative editing process is executed until receiving a user exit request and each iteration of the iterative editing process comprises:
        using a first machine learning model to generate a plurality of processed images, wherein each processed image corresponds to a distinct set of processing parameters;
        presenting the plurality of processed images to a user on a display;
        receiving a user response comprising (i) an indication of acceptance of one or more of the processed images, (ii) an indication of rejection of all of the processed images, or (iii) the user exit request;

using the plurality of processed images and the user response to train a second machine learning model to generate first model input parameters to the first machine learning model; and performing one or more clinical tasks using at least one of the processed images generated immediately prior to receiving the user exit request.

2. The method of claim 1, further comprising:
receiving the input image from an external source;
automatically performing the one or more image processing tasks on the input image to yield an initial processed image;
presenting the initial processed image to the user on the display;
in response to receiving a rejection of the initial processed image from the user, performing the iterative editing process.

3. The method of claim 1, wherein, during the iterative editing process, the first model input parameters are used as input to the first machine learning model.

4. The method of claim 1, wherein the iterative editing process further comprises:
using the second machine learning model to identify a most desirable option from among the plurality of processed images,
wherein the plurality of processed images are presented to the user on the display with a visual indication of the most desirable option.

5. The method of claim 1, wherein the iterative editing process further comprises:
using the second machine learning model to sort the plurality of processed images based on user preference,
wherein the plurality of processed images are presented to the user on the display in a sorted order.

6. The method of claim 1, further comprising:
identifying a region of interest within the input image,
wherein the first machine learning model is only applied to image data within the region of interest when generating the plurality of processed images.

7. The method of claim 6, wherein the region of interest is identified based on user selection of a region of the input image.

8. The method of claim 6, wherein the region of interest is automatically identified using the second machine learning model.

9. The method of claim 1, wherein the one or more image processing tasks comprise a segmentation of an anatomical object of interest from the input image.

10. The method of claim 1, wherein the one or more image processing tasks comprise a detection of one or more clinical indicators of interest present in the input image.

11. The method of claim 1, wherein the one or more image processing tasks comprise tracking of one or more objects of interest present in the input image.

12. The method of claim 1, wherein the one or more image processing tasks comprise registering the input image to one or more other images.

13. The method of claim 1, wherein the one or more image processing tasks comprise classifying the input image with one or more classification labels.

14. A computer-implemented method for processing an image, the method comprising:
receiving one or more images acquired from an image scanner device;
automatically generating an initial segmentation of an anatomical feature of interest by applying a segmentation algorithm to the one or more images;
presenting the initial segmentation to a user on a display;
in response to receiving a rejection of the initial segmentation from the user, performing an iterative segmentation process until receiving a user exit request comprising:
generating a plurality of alternative segmentations of the anatomical feature of interest by applying a first machine learning model to the one or more images using a plurality of first model parameters,
presenting the plurality of alternative segmentations to the user on the display,
receiving a user response comprising (i) an indication of acceptance of one or more of the alternative segmentations, (ii) an indication of rejection of all of the alternative segmentations, or (iii) the user exit request,
updating the plurality of first model parameters based on the user response, and
using the plurality of alternative segmentations and the user response to train a second machine learning model to learn one or more user segmentation preferences.

15. The method of claim 14, wherein the plurality of first model parameters are updated using the second machine learning model.

16. The method of claim 14, wherein the iterative segmentation process further comprises:
using the second machine learning model to identify a most desirable option from among the plurality of alternative segmentations,
wherein the plurality of alternative segmentations are presented to the user on the display with a visual indication of the most desirable option.

17. The method of claim 14, wherein the iterative segmentation process further comprises:
using the second machine learning model to sort the plurality of alternative segmentations based on user preference,
wherein the plurality of alternative segmentations are presented to the user on the display in a sorted order.

18. A system for processing images comprising:
a display;
one or more processors; and
a non-transitory, tangible computer-readable medium holding instructions executable by the one or more processors for performing a method comprising:
performing one or more image processing tasks on an input image using an iterative editing process, wherein the iterative editing process is executed until receiving a user exit request and each iteration of the iterative editing process comprises:
using a first machine learning model to generate a plurality of processed images, wherein each processed image corresponds to a distinct set of processing parameters;
presenting the plurality of processed images to a user on the display;
receiving a user response comprising (i) an indication of acceptance of one or more of the processed images, (ii) an indication of rejection of all of the processed images, or (iii) the user exit request;
using the plurality of processed images and the user response to train a second machine learning model to generate first model input parameters to the first machine learning model; and
following the iterative editing process, performing at least one clinical task using at least one of the processed images generated immediately prior to receiving the user exit request.

\* \* \* \* \*